United States Patent
Niznick (12) Patent No.: US 6,287,117 B1
(45) Date of Patent: Sep. 11, 2001

(54) ENDOSSEOUS DENTAL IMPLANTS INCLUDING A HEALING SCREW AND AN OPTIONAL IMPLANT EXTENDER

(75) Inventor: Gerald A. Niznick, Las Vegas, NV (US)

(73) Assignee: Sulzer Dental Inc., Houston, TX (US)

( * ) Notice: Subject to any disclaimer, the term of this patent is extended or adjusted under 35 U.S.C. 154(b) by 0 days.

(21) Appl. No.: 09/298,258

(22) Filed: Apr. 22, 1999

(51) Int. Cl.[7] .................................................. A61C 8/00

(52) U.S. Cl. ............................................................. 433/173

(58) Field of Search .................................. 433/173, 174, 433/175, 176

(56) References Cited

U.S. PATENT DOCUMENTS

| | | |
|---|---|---|
| 4,431,416 | 2/1984 | Niznick . |
| 4,492,577 | 1/1985 | Farris et al. . |
| 4,547,157 | 10/1985 | Driskell . |
| 4,600,388 | 7/1986 | Linkow . |
| 4,645,453 | 2/1987 | Niznick . |
| 4,661,066 | 4/1987 | Linkow et al. . |
| 4,713,003 | 12/1987 | Symington et al. . |
| 4,713,004 | 12/1987 | Linkow et al. . |
| 4,722,688 | 2/1988 | Lonca . |
| 4,832,601 | 5/1989 | Linden . |
| 4,850,870 | 7/1989 | Lazzara et al. . |
| 4,854,872 | 8/1989 | Detsch . |
| 4,856,648 | 8/1989 | Krueger . |
| 4,856,994 | 8/1989 | Lazzara et al. . |
| 4,904,187 | 2/1990 | Zingheim . |
| 4,955,811 | 9/1990 | Lazzara et al. . |
| 4,960,381 | 10/1990 | Niznick . |
| 5,030,095 | 7/1991 | Niznick . |
| 5,061,181 | 10/1991 | Niznick . |
| 5,062,800 | 11/1991 | Niznick . |
| 5,078,607 | 1/1992 | Niznick . |
| 5,106,300 | 4/1992 | Voitik . |
| 5,108,288 | 4/1992 | Perry . |
| 5,116,225 | * 5/1992 | Riera .................................... 433/173 |
| 5,135,395 | 8/1992 | Marlin . |
| 5,145,371 | * 9/1992 | Jörnéus ................................. 433/173 |
| 5,152,687 | 10/1992 | Amino . |
| 5,169,309 | 12/1992 | Staubli et al. . |
| 5,213,502 | 5/1993 | Daftary . |
| 5,281,140 | 1/1994 | Niznick . |
| 5,297,963 | 3/1994 | Daftary . |
| 5,312,254 | * 5/1994 | Rosenlicht ............................ 433/173 |

(List continued on next page.)

FOREIGN PATENT DOCUMENTS

| | | |
|---|---|---|
| 0288444 | 10/1988 | (EP) . |
| 0323421 | 7/1989 | (EP) . |
| 2635455 | 2/1990 | (FR) . |
| 2199502 | 7/1988 | (GB) . |
| 8803391 | 5/1998 | (WO) . |

OTHER PUBLICATIONS

"rotational Accuracy of Implant Components for Single Tooth, Root Implants," Dental Implantology Update, vol. 2, No. 1, Jan. 1991.

Swede–vent Prosthetics–A Breakthrough for Branemak Implant Users, Core–vent, Feb. 1, 1994.

Primary Examiner—Ralph A. Lewis
(74) Attorney, Agent, or Firm—Patrick F. Bright (57) ABSTRACT

Root-form, endosseous dental implants for insertion into an opening in the jawbone of a patient include a body portion, a neck and/or neck/abutment portion above the body portion, and an internally-threaded shaft; a separate optional implant extender for placement atop the implant with a top surface that mimics the top surface of the implant, and includes a longitudinal passage that receives a healing screw, and a healing screw with a threaded distal end portion to pass through the longitudinal passage, engage the internal threads of the implant and hold the extender to the implant, or to cover the opening to the internally-threaded shaft of the implant where the optional extender is omitted.

11 Claims, 5 Drawing Sheets

U.S. PATENT DOCUMENTS

| | | |
|---|---|---|
| 5,316,476 | 5/1994 | Kauser . |
| 5,322,443 | 6/1994 | Beaty et al. . |
| 5,334,024 | 8/1994 | Niznick . |
| 5,336,090 | 8/1994 | Wilson, Jr. et al. . |
| 5,338,196 | 8/1994 | Beaty et al. . |
| 5,368,160 | 11/1994 | Leuschen et al. . |
| 5,427,527 | 6/1995 | Niznick . |
| 5,433,606 | 7/1995 | Niznick . |
| 5,513,989 * | 5/1996 | Crisio ................................ 433/173 |
| 5,571,017 | 11/1996 | Niznick . |
| 5,575,650 | 11/1996 | Niznick . |
| 5,622,500 | 4/1997 | Niznick . |
| 5,681,167 * | 10/1997 | Lazarof ............................... 433/174 |
| 5,733,124 * | 3/1998 | Kwan .................................. 433/173 |
| 5,873,720 * | 2/1999 | Jorneus et al. ...................... 433/173 |
| 5,885,079 | 3/1999 | Niznick . |
| 5,989,028 | 11/1999 | Niznick . |

\* cited by examiner

ENDOSSEOUS DENTAL IMPLANTS INCLUDING A HEALING SCREW AND AN OPTIONAL IMPLANT EXTENDER

This invention relates to root-form one-part and two-part endosseous dental implants for insertion into an opening in the jawbone of a patient that include a healing screw and an optional implant extender.

Such one-part implants include a neck/abutment portion that is sufficiently long to extend through the gum tissue atop such an opening; an internally-threaded shaft inside the implant; an optional implant extender, preferably about 1 to about 4 mm in length, that fits atop the neck/abutment portion; and a healing screw with a threaded shank of sufficient length to pass through a longitudinal passage inside the implant extender, and to engage the internally-threaded shaft inside the implant.

The healing screw holds the extender to the implant, and covers the proximal opening into the longitudinal passage of the extender. If the extender is omitted, the healing screw, upon insertion into the internally-threaded shaft of the implant, covers the opening into the shaft. In some embodiments, these extenders include a distal end portion that fits over the neck/abutment portion of the implants, and a top portion that replicates the top portion of the implants, at least where the healing screw seats upon the implant's top end, and, optionally, where an abutment would sit atop the implant.

Two-part dental implants include an implant and a separate abutment, and require a two-stage surgical protocol. The first stage comprises inserting an implant, such as the CORE-VENT®, SCREW-VENT®, MICRO-VENT®, BIO-VENT® and BRANEMARK® implants, into the jaw bone, and burying it beneath the mucosal gum tissue for a submerged healing period. See, generally, U.S. Pat. No. 4,960,381, whose contents are incorporated herein by reference as though fully set forth here. Such implants include an externally-threaded or unthreaded, tapered or untapered body portion, and an internally-threaded shaft, with an internally-threaded region of sufficient length to accommodate an optional implant extender, and a healing screw with a threaded shank of sufficient length to pass through a longitudinal passage inside the extender, and to engage the internal threads of the implant.

The second stage comprises exposing the top of the submerged implant to allow attachment of an abutment. The abutment has a portion that extends above the gum tissue to allow attachment of a prosthesis. Submerged body implants and even non-submerged implants with a body and neck are usually two-part implants, requiring attachment to the implant of a separate abutment to support a prosthesis.

Many two-part implants include, at the top, a wrench-engaging surface, such as an internal or external hex or spline. Such wrench-engaging surfaces may be used for insertion of threaded implants into an opening in a patient's jawbone, or for connection of one-part or multi-part, screw-retained abutments that engage the wrench-engaging surface to provide anti-rotational stability to the abutment. Such a connection provides a stable base for attachment of a cemented single tooth restoration. All of these implants include an internally-threaded shaft extending downwardly from the top of the implant, and terminating inside the implant. This shaft is of sufficient length, and includes a threaded region of sufficient length, to engage the threaded distal end of the healing screw with, or without an implant extender atop the implant. The overall length of these implants, whether one-part or two-part, is preferably at least about 8 mm, with the internally threaded shaft region of the internal shaft preferably at least about 4–5 mm in length, to accommodate the implant extender and healing screw.

The implant/implant extender/healing screw combination is preferably packaged in an enclosed vial with a stopper that engages all three parts of this combination, but the implant extender may be packaged alone or with a healing screw. Such a stopper includes, at its distal end, a multi-sided male member that fits snugly into multi-sided internal wrench-engaging surfaces of the implant. The stopper also includes a body portion that fits into, and frictionally engages, the opening into a vial for the implant. An external annular flange on the stopper seats on the rim of the vial opening at its proximal end. This stopper includes an internal passage from its proximal end that receives and frictionally or otherwise engages the healing screw and the implant extender. The extender may include a threaded region in its longitudinal passage to engage the threads on the shank of the healing-screw. The stopper then serves as a delivery tool for delivering the extender and healing screw together to an implant after its placement in a jawbone site.

The one-stage surgical protocol comprises inserting an implant, e.g., Straumann's ITI® implant or a Screw-Vent® II implant (see FIG. 1), with its cylindrical neck portion extending through the gum tissue at time of implantation, avoiding the need for a second stage of surgery. Such implants may have a neck portion alone that extends through the gum tissue, or a neck/abutment portion for support or retention of a prosthesis.

One-part, root-form, endosseous dental implants are disclosed in U.S. patent application Ser. No. 08/887,463, filed Jul. 2, 1997, in the United States Patent and Trademark Office. The contents of that application are incorporated herein by reference as though fully set forth here. Such one-part implants may include a body portion adapted to be inserted into an opening in a patient's jawbone, and to become attached directly to bone at that site through a process called osseointegration. The body portion of these implants may be wholly or partly externally threaded or unthreaded, as in the SCREW-VENT® or BIO-VENT® dental implants; may include a hollow basket structure, as in the CORE-VENT® dental implant; or a ledge-type structure, as in the MICRO-VENT® dental implant. Preferably, the body portion is similar to the body portion of the SCREW-VENT® implant. Preferably, such body portions are tapered, and have externally-threaded surfaces with outside/inside thread diameters of 3.3 mm/2.8 mm, 3.7 mm/3.2 mm, and 4.7 mm/4.2 mm.

The optional implant extenders increase the available jawbone placement options with both one-part root-form endosseous dental implants and two-part root-form endosseous dental implants. With one-part root-form endosseous dental implants, the dental professional can place the implant in a jawbone site with the neck or neck/abutment portion of the implant projecting above the crestal bone and through the mucosal tissue atop the site, thus avoiding the trauma and cost of the second surgery required with two-part implants. Such placement in posterior jawbone sites may be satisfactory, but is likely less desirable in anterior jawbone sites. For such sites, the dental professional can use a one-part, root-form, endosseous dental implant by placing the implant in the jawbone site such that the neck or neck/abutment portion does not extend above the mucosal tissue, and then use the optional implant extender to extend the implant above the mucosal tissue.

Following healing, the extender can be removed, and a tapered abutment or abutment adapter attached to the implant to allow fabrication of a crown with its margin below the tissue for aesthetics. Since the implant extenders have a top surface that substantially mimics or replicates the top surface of the implant, a dental professional's restoration options are unimpeded by differences between the top surface of the implant itself and the top surface of the extender for attachment of a ball or tapered screw abutment.

The wrench-engaging surfaces, internally-threaded shaft, or both may be connected to a one-part or multi-part abutment, whether ball-shaped, tapered (straight or angled), atop the neck/abutment portion of a one-part implant. Such abutments may provide anti-rotational support, or retention for cemented restorations or overdentures, thus expanding clinical applications.

External wrench-engaging surfaces may be multi-sided, multi-faceted or splined projections (as, for example, in Calcitek's endosseous, root-form, external spline or Axel Kirsch's endosseous, root-form, internal spline or grooved (cam) dental implants) that are adapted to hold, twist or turn the implant for insertion, or for connection to multi-part abutment extensions. Such features are preferably located at, and surround, the opening to the internally-threaded shaft.

The external projection, atop an implant in embodiments that include external wrench-engaging facets or sides, may (but need not) be tapered slightly, preferably in the range of about 1 to about 2 degrees. Where tapered, the projection provides a friction-fit attachment of an abutment for stable, anti-rotational support of a cemented, single-tooth restoration. See U.S. Pat. No. 5,433,606, incorporated herein by reference, for a description of such tapered projections. Preferably, this projection has a length of about 0.5 mm to about 1.5 mm and a diameter in the range of about 2.0 mm to about 3.0 mm, and more preferably about 2.5 mm.

BRIEF DESCRIPTION OF THE DRAWINGS

This invention can better be understood by reference to the drawings which are as follows.

DETAILED DESCRIPTION OF THE PREFERRED EMBODIMENTS

Figure 1:
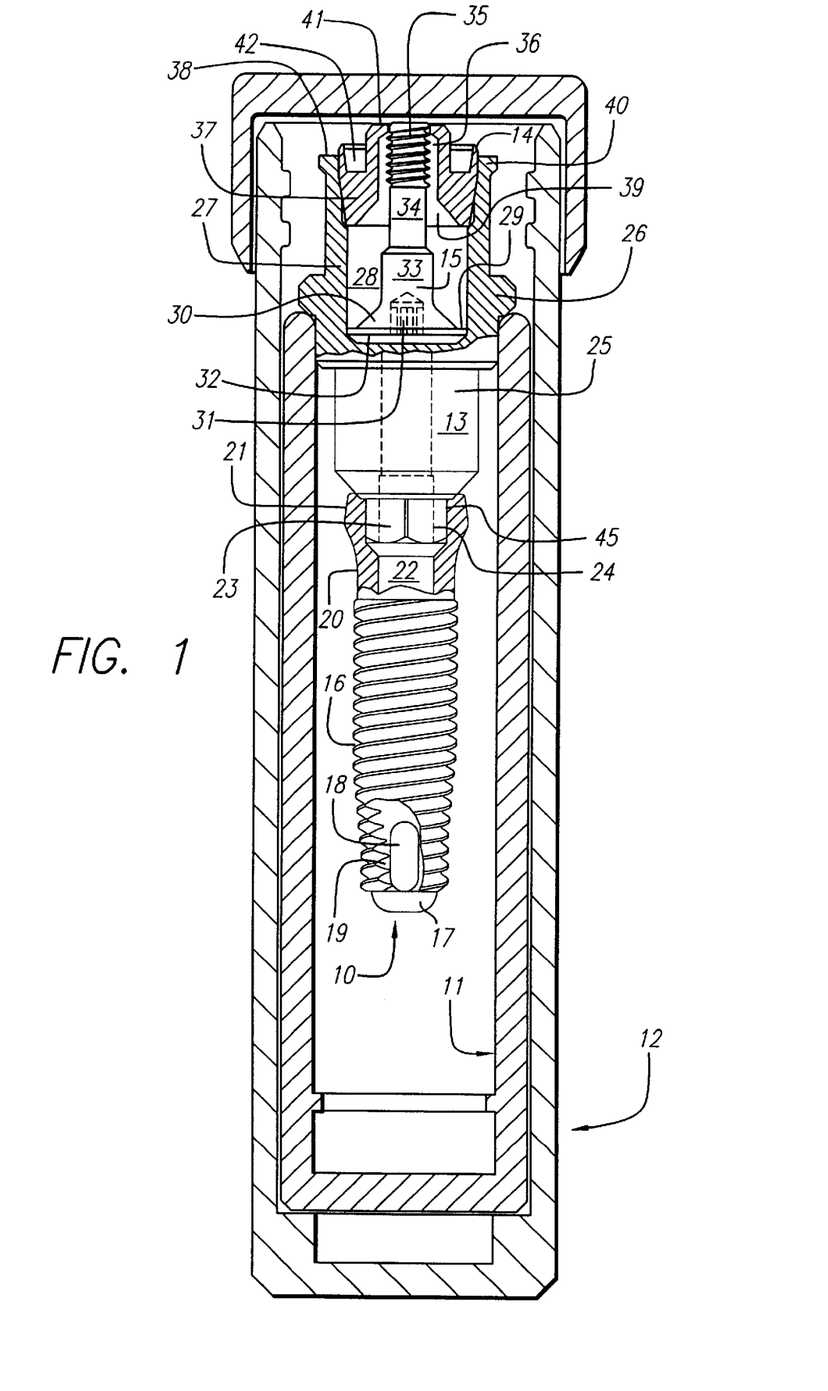
FIG. 1 shows a one-part endosseous dental implant with an externally-threaded, tapered external body, a through-hole in the wall of the implant near its distal end, self-tapping threads near its distal end, and, at its proximal end, an outwardly flaring elongated shoulder above the threaded body region that is up to about 2–4 mm in length, internal wrench-engaging surfaces, and an internally-threaded passage, packaged with an implant extender having a threaded longitudinal internal passage, a top end that substantially mimics or duplicates the top end of the implant, and with a healing screw having an elongated, distally threaded portion.

FIG. 1 shows endosseous dental implant 10 with an externally-threaded body portion 16, apical hole 17, transverse through-hole 18, and self-tapping cutting threads 19. Atop the threaded body portion of implant 10 are outwardly-tapering neck portion 20 and abutment portion 21. Inside implant 10 is internally-threaded shaft 22. At the proximal end of shaft 22 are internal wrench-engaging surfaces 23. Inserted into wrench-engaging surfaces 23 is packaging stopper 13. Stopper 13 includes complementary, multi-sided, male member 24 at its distal end, body portion 25, annular flange 26, and cylindrical wall portion 27.

Inside stopper 13 is internal shaft 28 which includes surface 29 for receiving tapered proximal end portion 30 of healing screw 15. Healing screw 15 includes tapered proximal end portion 30, internal tool-engaging or wrench-engaging surfaces 31 projecting downwardly into end portion 30 from surface 32, shank 33, and threaded shank portion 34 that includes distal threads 35 on its external surface. Threaded shank portion 34 projects into longitudinal passage 36 inside implant extender 14. Extender 37 is friction-fit into opening 38 at the top of stopper 13. Implant extender 14 includes, at its proximal end, internal chamfered region 39, outwardly tapering external wall 40, projection 41 at its distal end, and, surrounding projection 41, trepanned hole 42. The top end of extender 14 substantially mimics the top end of implant 10, including those surfaces upon which an abutment, if any, would sit.

Trepanned hole 42 fits over and rests upon external surface 21 of implant 10 with projection 41 extending into the area surrounded by wrench-engaging surfaces 23. Healing screw 15 passes through longitudinal passage 36 of extender 14 and then into internally-threaded passage 22 of implant 10.

When screwed into place atop implant 10, healing screw 15 holds extender 14 in place atop implant 10. If the extender 14 is omitted, healing screw 15 screws into internal passage 22 of implant 10 sufficiently far such that surface 30 seats on internal chamfered region 45 inside implant 10. Alternatively, when extender 14 is in place atop implant 10, healing screw 15 is screwed into internally-threaded shaft or passage 22 of implant 10 until surface 30 of screw 15 seats on surface 39 of extender 14.

Figure 2:
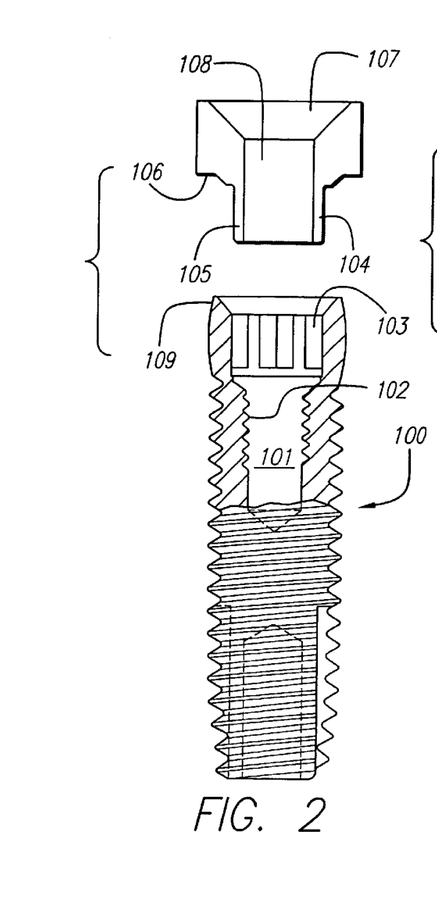
FIG. 2 shows an externally threaded Screw-Vent-type endosseous dental implant with a second embodiment of an implant extender.
Figure 3:
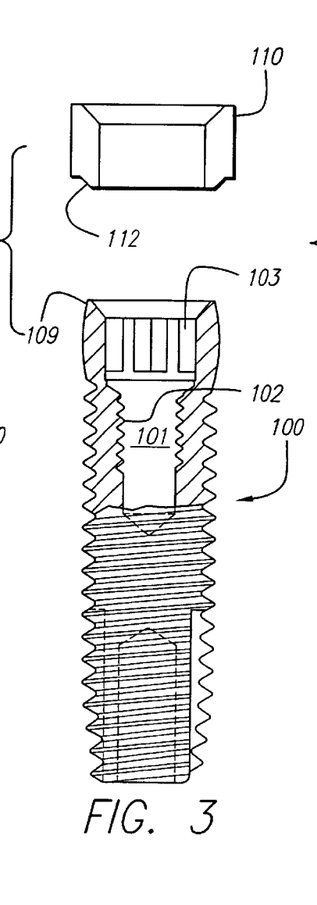
FIG. 3 shows the implant of FIG. 2 with a third embodiment of an implant extender.
Figure 5:
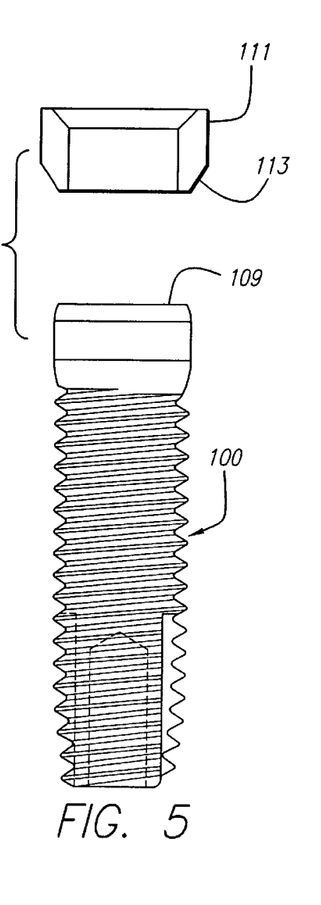
FIG. 5 shows the implant of FIGS. 2 and 3, with a fourth embodiment of an implant extender.

FIGS. 2, 3, and 5 show externally-threaded endosseous dental implant 100 including internally-threaded shaft 101 and with wrench-engaging surfaces 103 and threads 102 inside shaft 101.

In FIG. 2, implant extender 104 includes distal portion 105, flange surface 106, chamfered internal region 107 and internal passage 108. With extender 104 atop implant 100, portion 105 extends into internally-threaded shaft 101, and surface 106 sits atop surface 109 at the top of implant 100. Healing screw 15 (see FIG. 1) passes through internal passage 108, with surface 30 seating itself on chamfered region 107, and threaded shank portion 35 engaging internal threads 102 inside implant 101.

In the embodiment shown in FIGS. 3 and 5, implant extenders 110 and 111, respectively, each include internal passages such as 108 shown in extender 104. Extender 110 includes surface 112 that seats upon surface 109 of implant 100; extender 111 includes surface 113 that seats upon surface 109 of implant 100 in FIG. 5. Healing screw 15 then passes through the internal passage in these extenders such that its threads 35 can engage the internal threads 102 inside internally-threaded shaft 101.

Figure 4:
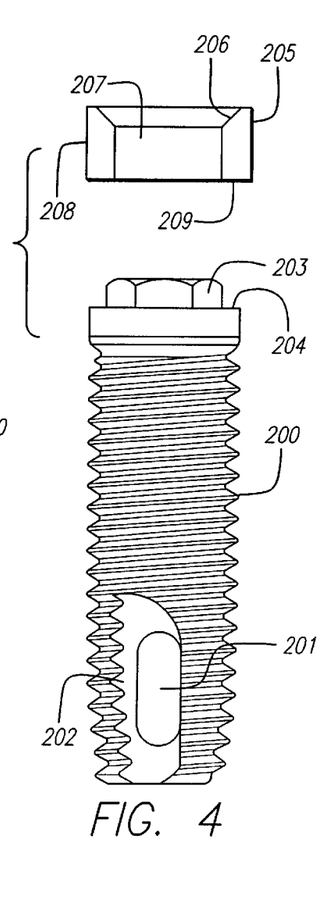
FIG. 4 shows a Swede-Vent type, externally-threaded, endosseous dental implant with external wrench-engaging surfaces and an internally-threaded shaft, with a fourth embodiment of an implant extender.

FIG. 4 shows externally-threaded endosseous dental implant 200 with through-hole 201 and self-cutting threads 202 at the distal end of the implant 200. Atop distal implant 200 is multi-sided wrench-engaging surface 203 external to the implant and projecting from surface 204. Implant extender 205 includes a chamfered surface 206, internal passage 207 and cylindrical external wall surface 208. With extender 205 seated on surface 204, healing screw 15 can pass through external passage 207 and surface 30 of screw 15 can seat on surface 206. Threads 35 can then engage threads (not shown) internal to implant 200.

Figure 6A:
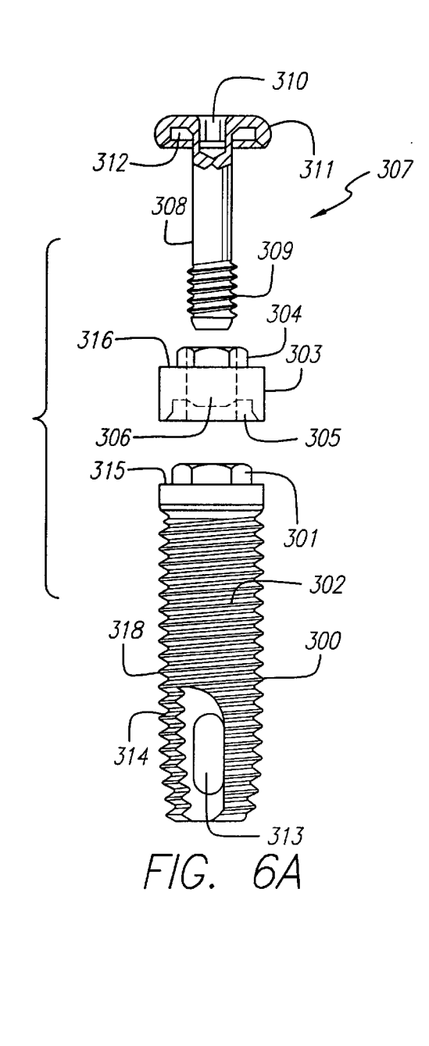
FIG. 6A shows an externally thread endosseous dental implant with external wrench-engaging means, an optional implant extender and a healing screw for use with the extender/implant combination or with the implant alone.

FIG. 6A shows endosseous dental implant 300 with external threads along the length of its body portion 318 and, atop implant 300, upwardly projecting, six-sided external projection 301 that provides wrench-engaging surfaces to engage an abutment. Implant 300 also includes self-tapping threads 314 and through-hole 313 near its distal end, and an internally-threaded shaft.

Above implant 300 is optional implant extender 303. Extender 303 includes internal longitudinal passage 306, and on its top surface, six-sided projection 304. At its distal end, extender 303 includes cavity 305 that is of a size and shape sufficient to cover projection 301 and rest upon surface 315 atop implant 300. Extender 303 has a top surface that mimics the surfaces 315 and 301 of implant 300 such that, when extender 303 is in place atop implant 300, extender 303 effectively lengthens implant 300, increasing the feasible surgical placement options for this implant, as shown and explained below in connection with FIGS. 7A and 7B.

Healing screw 307 includes unthreaded shank portion 308 and distal threaded shank portion 309, head portion 311, proximal tool engaging passage 310, and, below head portion 311, annular trepanned hole 312. Screw 307 is of sufficient length to engage the internal threads inside implant 300, with or without extender 303 in place atop implant 300.

Figure 6B:
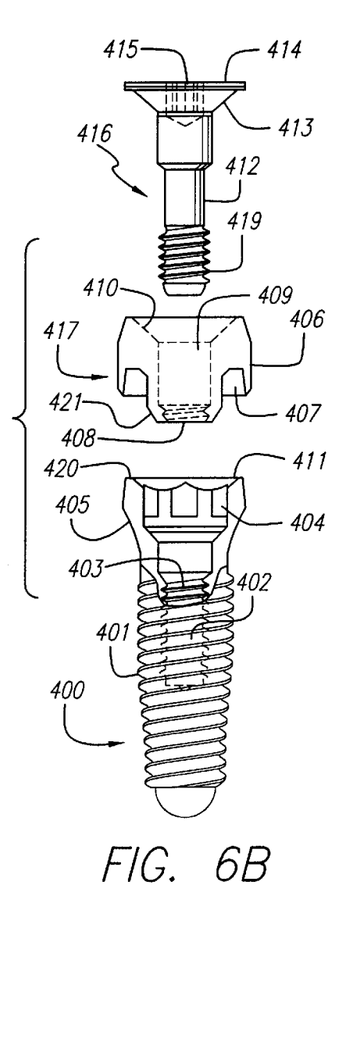
FIG. 6B shows an endosseous dental implant with a tapered externally threaded body, internal wrench engaging surfaces and an internally threaded shaft, together with an optional implant extender and a healing screw for use with the implant/extender combination or with the implant alone.
Figure 6C:
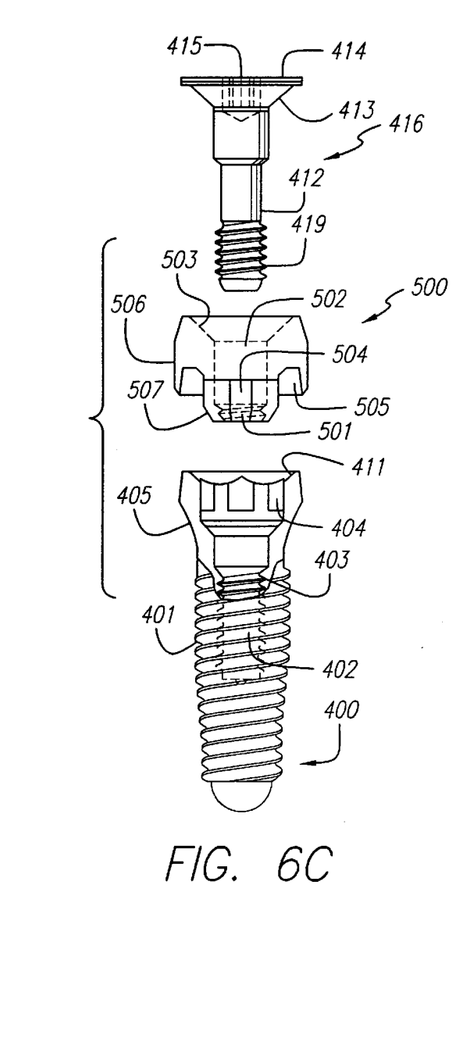
FIG. 6C shows the implant depicted in FIG. 6B with the healing screw depicted in FIG. 6B but with an implant extender that includes an external, multi-sided surface which is complementary to and engages the internal wrench-engaging surfaces of the implant when the extender is in place atop the implant.

FIGS. 6B and 6C show endosseous dental implant 400 with external threads 401 on the body of implant 400, unthreaded neck/abutment portion 405 atop external threads 401, and internal passage 402 with internal threads 403, internal wrench-engaging surfaces 404, and chamfered region 411 at or near the top of the passage 402.

FIGS. 6B and 6C also show healing screw 416 that includes unthreaded shank portion 412, threaded distal shank portion 419, head member 414, internal tool-engaging passage 415 and, on the undersurface of head portion 414, tapered annular portion 413.

FIG. 6B also shows optional implant extender 417 with its internal longitudinal passage 409, internal threads 408 and internal chamfered region 410. External surface 406 of extender 417 mimics, or substantially duplicates, the top surface of neck/abutment portion 405 of implant 400. When in place atop implant 400, trepanned hole 407 sits over top surface 420 of implant 400 with projection 421 of extender 417 fitting into internal passage 402. Healing screw 416 then passes through longitudinal passage 409, through threads 408 and into engagement with internal threads 403 inside implant 400. Undersurface 413 of head portion 414 is of a size and shape appropriate to sit on, and conform to, surface 410 of extender 417, or on surface 411 of implant 417 when extender 417 is not in use.

FIG. 6C shows healing screw 416 and implant 400 used with optional implant extender 500. Extender 500 includes internal longitudinal passage 502, internal threads 501, external wall surface 506 that mimics or substantially duplicates the top surface of implant 400, and includes, on projection 507, multisided surface 504 that fits within and engages, anti-rotationally, the multi-sided internal wrench-engaging surfaces 404 of implant 400.

Figure 7A:
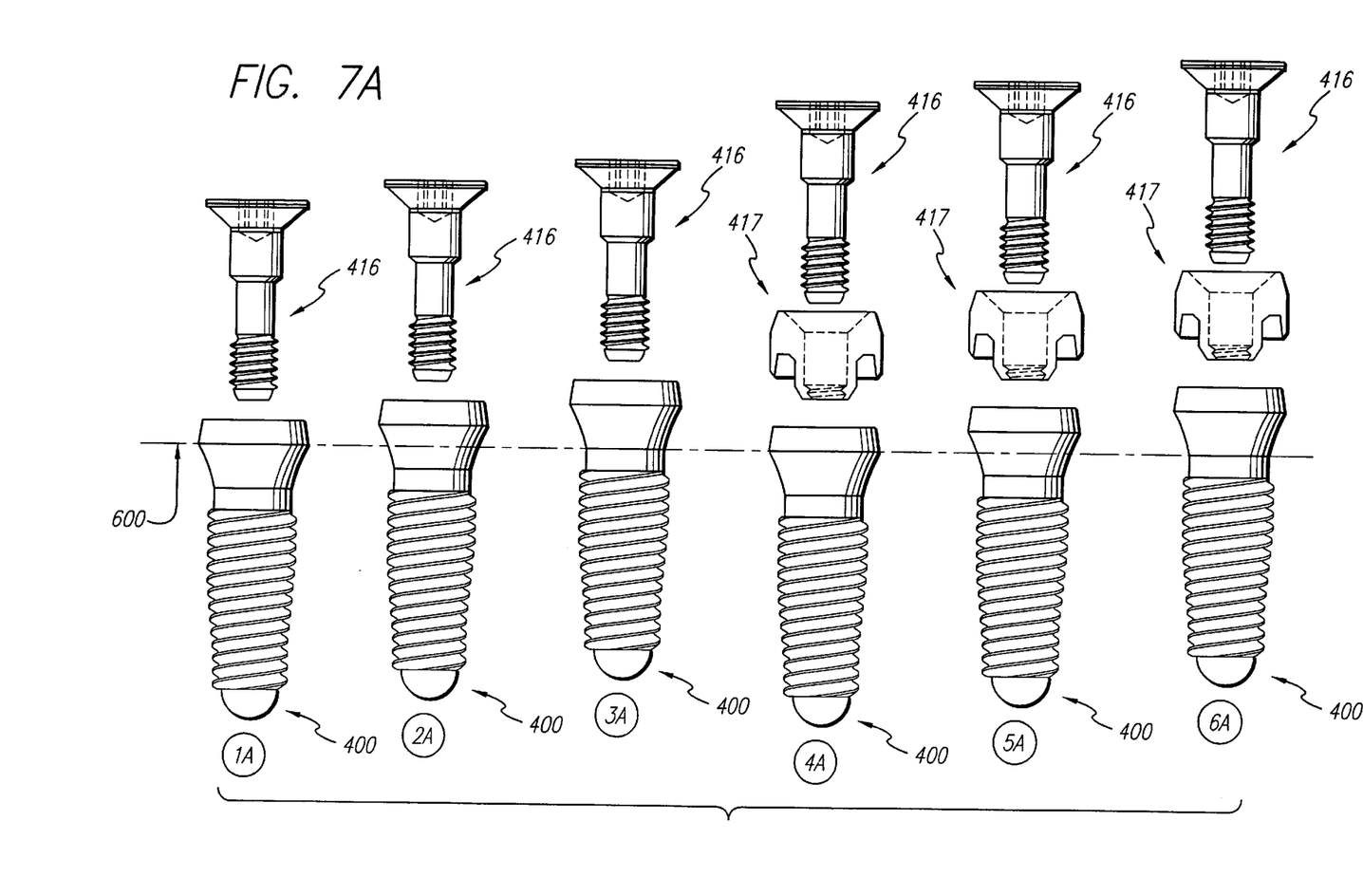
FIG. 7A shows the jawbone placement options available with an externally threaded, tapered, endosseous dental implant when used with a healing screw alone and when used with both a healing screw and an optional implant extender (the dental implant, healing screw and optional implant extender shown in FIGS. 7A and 7B is the implant, optional extender and healing screw depicted in FIG. 6B above.).
Figure 7B:
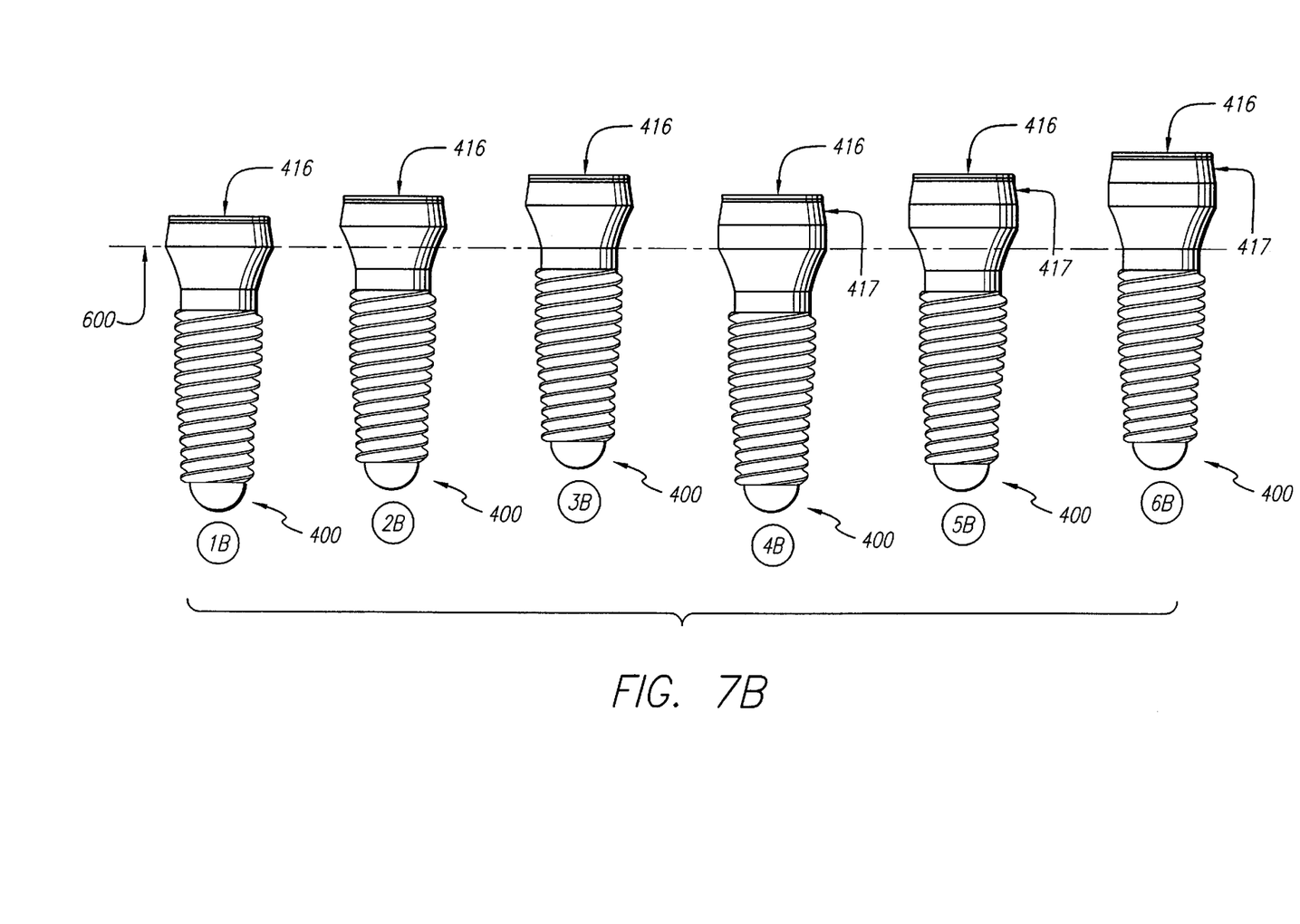

FIGS. 7A and 7B show how the implant/implant extender/healing screw combination provides a multitude of jawbone implant placement options to a dental professional. FIGS. 7A and 7B show schematically the crest 600 of a patient's jawbone, and show that this combination, with or without the optional implant extender, permits placement in a patient's jawbone with one millimeter of the implant extending above the crest of bone level 600 (1A views), three millimeters above crest 600 (2A views), or five millimeters above crest 600 (3A views). FIGS. 7A and 7B also show that, with the implant extender 417 in place atop implant 400, where as here the extender mimics or substantially duplicates the top portion of implant 400, the overall length of the implant can be extended by up to an additional three millimeters. As FIG. 7B shows, healing screw 416 seats in, and conforms to, the chamfered region at the opening to the internal passage of implant 400, with the extender not in use (see 1B, 2B and 3B views), or into the chamfered region at the opening into the longitudinal passage of the implant extender (see 4B, 5B and 6B views).

What is claimed is:

1. An endossecous, root-form dental implant for insertion into an opening in the jawbone of a patient including:

a body portion;

an internally-threaded shaft extending into said implant from the top surface of said implant;

a healing screw comprising a head portion joined to a threaded shank portion, said head portion having a size and shape sufficient to cover a proximal opening into said shaft;

an implant extender having a top surface that substantially replicates the top surface of said implant, said extender having a distal end portion of a size and shape sufficient to engage and seat upon said implant atop said body portion, said extender including an internal longitudinal passage of sufficient size and shape to permit the threaded distal end portion of said healing screw to pass through said longitudinal passage, said passage including an opening in its proximal end having a size and shape complementary to the size and shape of the head portion of said healing screw;

said internally-threaded shaft of said implant having a threaded region sufficiently long to engage said threaded distal end portion of said healing screw with said implant extender in place atop said implant and with the undersurface of the head portion of said healing screw covering the opening to said extender or, if said extender is absent, covering the opening into said internally-threaded shaft of said implant.

2. The implant of claim 1 further comprising internal wrench-engaging surfaces inside said internally-threaded shaft, or external wrench-engaging surfaces projecting from the top of said implant.

3. The implant of claim 1 or claim 2 wherein the top of said neck portion and/or said abutment portion has a size and shape adapted to form a sealed margin with a prosthetic attachment.

4. The implant of claim 1 or claim 2 wherein said body portion is externally-threaded.

5. The implant of claim 2 wherein said wrench-engaging surfaces project from the top of said implant and have 4 to 8 flat, contiguous sides, or a plurality of splines.

6. An endosseous, root-form dental implant for insertion into an opening in the jawbone of a patient including:

a body portion including a neck portion formed above said body portion and including a top surface;

an internally-threaded shaft extending into said implant from the top surface of said implant;

a healing screw comprising a head portion joined to a threaded shank portion, said head portion having a size and shape sufficient to cover a proximal opening into said shaft;

an implant extender having a top surface that substantially replicates the top surface of said implant, said extender having a distal end portion of a size and shape sufficient to engage and conform to the top surface of said implant, said extender including an internal longitudinal passage of sufficient size and shape to permit the threaded distal end portion of a healing screw to pass through said longitudinal passage, said passage including an opening in its proximal end having a size and shape complementary to the size and shape of the head of said healing screw;

said internally-threaded shaft of said implant having a threaded region sufficiently long to engage said threaded distal end portion of said healing screw with said implant extender in place atop said implant and with the undersurface of the head portion of said healing screw covering the opening to said extender or, if said extender is absent, covering the opening into said internally-threaded shaft of said implant.

7. The implant of claim 6 further comprising an internal wrench-engaging surfaces inside said internally-threaded shaft, or external wrench-engaging surfaces projecting from the top of said implant.

8. The implant of claim 7 wherein said wrench-engaging surfaces project from the top of said implant and have from 4 to 8 flat, contiguous sides, or a plurality of splines.

9. The implant of claim 6 or claim 7 wherein said body portion is externally-threaded.

10. The implant of claim 6 wherein said top surface has a size and shape adapted to form a sealed margin with a prosthetic attachment.

11. The implant of claim 1 or claim 6 further comprising internal wrench-engaging surfaces inside said internally-threaded shaft, said optional implant extender having a distal portion of a size and shape appropriate to fit into said internally-threaded shaft, and a body portion that fits over the top surface and at least part of said neck portion of said implant.

* * * * *